US007270818B2

(12) United States Patent
Averback

(10) Patent No.: US 7,270,818 B2
(45) Date of Patent: Sep. 18, 2007

(54) PHARMACEUTICALLY ACTIVE AGENTS THAT IMPEDE THE FORMATION OF AMYLOID BY IMPEDING THE GENESIS OR GROWTH OF DMS

(75) Inventor: Paul Averback, Beaconsfield (CA)

(73) Assignee: Nymox Corporation, Saint Laurent, Quebec (CA)

( * ) Notice: Subject to any disclaimer, the term of this patent is extended or adjusted under 35 U.S.C. 154(b) by 582 days.

(21) Appl. No.: 10/186,681

(22) Filed: Jul. 2, 2002

(65) Prior Publication Data

US 2003/0083298 A1 May 1, 2003

Related U.S. Application Data

(62) Division of application No. 09/017,689, filed on Feb. 3, 1998, now Pat. No. 6,413,940.

(60) Provisional application No. 60/038,694, filed on Feb. 7, 1997.

(51) Int. Cl.
*A61K 39/395* (2006.01)

(52) U.S. Cl. .................................................. 424/152.1

(58) Field of Classification Search ..................... None
See application file for complete search history.

(56) References Cited

U.S. PATENT DOCUMENTS

| | | | |
|---|---|---|---|
| 4,540,564 | A | 9/1985 | Bodor |
| 4,816,416 | A | 3/1989 | Averback |
| 4,919,915 | A | 4/1990 | Averback |
| 5,231,170 | A | 7/1993 | Averback |

FOREIGN PATENT DOCUMENTS

| | | | |
|---|---|---|---|
| WO | WO90/09789 | * | 9/1990 |
| WO | WO95/16917 | * | 6/1995 |

OTHER PUBLICATIONS

Small et al. 2000. Proc Natl Acad Sci USA 97:6037-6042.*
Vickers 2002. Drugs Aging 19:487-494.*
Cooper et al. 1995. Current Protocols in Immunology 2.4.1-2.4.9.*
Finney, "Molecular Cloning of PCR Products," *Current Protocols in Molecular Biology* (1987), Ausubel et al., Eds., p. 15.7.1, John Wiley & Sons, New York.
Kono et al., "Is it Useful to Manage Alzheimer's Disease as Two Clinical Subtypes: Early Onset and late Onset Subtypes?," *Basic clinical and Therapeutic Aspects of Alzheimer's and Parkinson's Diseases* (1990), vol. 2, pp. 143-146, Plenum Press, New York.
Brandt et al., "Relation of Age of Onset and Duration of Illness to cognitive Functioning in Alzheimer's Disease," *Neuropsychiatry, Neuropsychology, and Behavioral Neurolgy* (1989), vol. 2, No.2, pp. 93-101.
Stein et al., "Oligodeoxynucleotides as Inhibitors of Gene Expression: A Review," *Cancer Research* (1988), vol. 48, pp. 2659.-2668.
Saiki et al., "Primer-Directed Enzymatic Amplification of DNA with a Thermostable DNA Polymerase," *Science* (1988), vol. 239, pp. 487-491.
Hara, "Microscopic Globular Bodies in the Human Brain," *Journal of Neuropathology and Experimental Neurology* (1986), vol. 45, No. 2, pp. 169-178.
Knesivich et al., "Aphasia, Family History, and the Longitudinal course of Senile Dementia of the Alzheimer Type," *Psychiatry Res.* (1984), vol. 14, pp. 255-263.
Averback, "Dense Microspheres in Normal Human Brain," *Acta Neuropathol.* (1983), vol. 61, pp. 148-152.
Tomilinson et al., "Observations on the Brains of Demented Old People," *Journal of Neurological Sciences* (1970), vol. 11, pp. 205-242.
Tomilinson et al., "Observations on the Brains of Non-Demented Old People," *Journal of Neurological Sciences* (1968), vol. 11, pp. 331-356.
Blessed et al., "The Association Between Quantitative Measures of Dementia and of Senile Change in the Cerebral Grey Matter of Elderly Subjects," *British Journal of Psychiatry* (1968), vol. 114, pp. 797-811.
Paterson et al., "Structural gene identification and mapping by DNA-mRNA hybrid-arrested cell-free translation," *Proc. Natl. Acad. Sci. USA* (1977), vol. 74, pp. 4370-4374.
Corsellis, "Aging and Dementias," *Greenfield's Neuropatholgy* (1976), pp. 796-848, Edward Arnold, London, United Kingdom.
Rojanasakul, "Antisense Oligonucleotide Therapeutics: Drug Delivery and Targeting," *Advanced Drug Delivery Reviews* (1996), vol. 18, pp. 115-131.
Gura, *Science* (1995), vol. 270, pp. 575-577.
Minturn et al., *J. Neurosci.* (1995), vol. 15, pp. 6757-6766.
Gaetano et al., *JBC* (1997), vol. 272, pp. 12195-12201.
Goshima et al., *Nature* (1995), vol. 376, pp. 509-514.
Hawkins et al., *Biochemistry* (1993), vol. 32, pp. 9985-9993.
Murakami et al., *Gene* (1996), vol. 179, pp. 245-249.
Izzo et al., *Eur. J. Biochem.* (1988), vol. 174, pp. 569-578.
Uhlmann et al., *Chem. Rev.* (1990), vol. 90, pp. 544-584.
Harding et al., *JBC* (1986), pp. 8547-8555.

* cited by examiner

*Primary Examiner*—Robert C. Hayes
*Assistant Examiner*—Daniel E. Kolker
(74) *Attorney, Agent, or Firm*—Foley & Lardner LLP

(57) ABSTRACT

Methods of treating and/or prophylaxis Alzheimer's disease by preventing the formation of cerebral amyloid due to the growth and disruption of dense microspheres (DMS) are disclosed utilizing medicaments that are effective in preventing or inhibiting the growth and disruption of DMS.

1 Claim, 14 Drawing Sheets

```
                    SEQUENCE LISTING

(1) GENERAL INFORMATION:

   (iii) NUMBER OF SEQUENCES: 7

(2) INFORMATION FOR SEQ ID NO: 1:

     (i) SEQUENCE CHARACTERISTICS:
          (A) LENGTH: 27 amino acids
          (B) TYPE: amino acid
          (C) STRANDEDNESS: <Unknown>
          (D) TOPOLOGY: linear

    (ii) MOLECULE TYPE: protein

    (xi) SEQUENCE DESCRIPTION: SEQ ID NO: 1:

Ile Leu Asp Leu Gly Ile Thr Gly Pro Glu Gly His Val Leu Ser Arg
1               5                   10                  15

Pro Glu Glu Val Glu Ala Glu Ala Val Asn Lys
            20                  25

(2) INFORMATION FOR SEQ ID NO: 2:

     (i) SEQUENCE CHARACTERISTICS:
          (A) LENGTH: 18 amino acids
          (B) TYPE: amino acid
          (C) STRANDEDNESS: <Unknown>
          (D) TOPOLOGY: linear

    (ii) MOLECULE TYPE: protein

    (xi) SEQUENCE DESCRIPTION: SEQ ID NO: 2:

Ile Ala Val Gly Ser Asp Ala Asp Leu Val Ile Trp Asp Pro Asp Ser
1               5                   10                  15

Val Lys

(2) INFORMATION FOR SEQ ID NO: 3:

     (i) SEQUENCE CHARACTERISTICS:
          (A) LENGTH: 20 amino acids
          (B) TYPE: amino acid
          (C) STRANDEDNESS: <Unknown>
          (D) TOPOLOGY: linear

    (ii) MOLECULE TYPE: protein

    (xi) SEQUENCE DESCRIPTION: SEQ ID NO: 3:

Ile Val Asn Asp Asp Gln Ser Phe Tyr Ala Asp Ile Tyr Met Glu Asp
1               5                   10                  15

Gly Leu Ile Lys
            20

(2) INFORMATION FOR SEQ ID NO: 4:

     (i) SEQUENCE CHARACTERISTICS:
          (A) LENGTH: 28 amino acids
          (B) TYPE: amino acid
```

-continued

```
        (C) STRANDEDNESS: <Unknown>
        (D) TOPOLOGY: linear

   (ii) MOLECULE TYPE: protein

   (xi) SEQUENCE DESCRIPTION: SEQ ID NO: 4:

Asn Ile Ile Leu Glu Glu Gly Lys Asp Ile Leu Val Gly Asp Val Gly
1               5                   10                  15

Gln Thr Val Asp Asp Pro Tyr Ala Thr Thr Phe Val
            20                  25


(2) INFORMATION FOR SEQ ID NO: 5:

    (i) SEQUENCE CHARACTERISTICS:
        (A) LENGTH: 18 amino acids
        (B) TYPE: amino acid
        (C) STRANDEDNESS: <Unknown>
        (D) TOPOLOGY: linear

   (ii) MOLECULE TYPE: protein

   (xi) SEQUENCE DESCRIPTION: SEQ ID NO: 5:

Gly Ile Val Asp Gln Ser Gln Gln Ala Tyr Gln Glu Ala Phe Glu Ile
1               5                   10                  15

Ser Lys


(2) INFORMATION FOR SEQ ID NO: 6:

    (i) SEQUENCE CHARACTERISTICS:
        (A) LENGTH: 18 amino acids
        (B) TYPE: amino acid
        (C) STRANDEDNESS: <Unknown>
        (D) TOPOLOGY: linear

   (ii) MOLECULE TYPE: protein

   (xi) SEQUENCE DESCRIPTION: SEQ ID NO: 6:

Val Asn Pro Thr Val Phe Phe Asp Ile Ala Val Asp Gly Glu Pro Leu
1               5                   10                  15

Gly Arg


(2) INFORMATION FOR SEQ ID NO: 7:

    (i) SEQUENCE CHARACTERISTICS:
        (A) LENGTH: 30 amino acids
        (B) TYPE: amino acid
        (C) STRANDEDNESS: <Unknown>
        (D) TOPOLOGY: linear

   (ii) MOLECULE TYPE: protein

   (xi) SEQUENCE DESCRIPTION: SEQ ID NO: 7:

Thr Val Pro Pro Ala Val Thr Gly Ile Thr Phe Leu Ser Gly Gly Glu
1               5                   10                  15

Ser Glu Glu Glu Ala Ser Ile Asn Leu Asn Ala Ile Asn Lys
            20                  25                  30
```

PHARMACEUTICALLY ACTIVE AGENTS THAT IMPEDE THE FORMATION OF AMYLOID BY IMPEDING THE GENESIS OR GROWTH OF DMS

This application is a divisional of application ser. No. 09/017,689 filed on Feb. 3, 1998, now U.S. Pat. No. 6,431,940, which claims benefit of provisional application Ser. No. 60/038,694 filed on Feb. 7, 1997.

BACKGROUND OF THE INVENTION

1. Field of the Invention

The present invention relates to the identification of compounds that act, at physiologically-compatible levels, to inhibit the formation of Alzheimer senile amyloid plaques by inhibiting the genesis and/or growth of dense microspheres (DMS). More specifically, the present invention relates to pharmaceutically active agents that impede formation of Alzheimer senile amyloid plaques in vivo, and to a method for the screening of compounds which possess this activity.

2. Description of Related Art

There is no effective therapy for cerebral amyloidosis, (the accepted cause of Alzheimer's disease), which almost invariably has a fatal outcome following the onset of amyloid deposits. For example, Alzheimer's disease is estimated to be the fourth or fifth leading cause of death in North Americans.

A universally accepted indicator of cerebral amyloidosis is the accumulation of large numbers of lesions, so-called "senile plaques," that are comprised in large part of amyloid fibrils. Senile plaques are spherical, ranging from 10 to 200 μm in diameter, that are found occasionally in aged adult cerebral cortex but are present in large numbers in Alzheimer-affected cortex.

The utilizing of materials found in human brain (normal or Alzheimer-affected) that are not already amyloid, and of transforming them into amyloid, has been documented in the literature. There was also description in the art of an experimental system, derived exclusively from human materials, that was characterized by the clinical manifestations of Alzheimer's disease. Because the presence of amyloid is the most qualitatively and quantitatively specific indication of senile-plaque formation, most specialists agree that reproduction of amyloid fibrils experimentally from precursor materials which are extracted, activated, or otherwise derived from human brain constitutes the best available evidence linking an agent or precursor to the progression of cerebral amyloidosis.

With the recognized importance of an experimental system that would permit testing for such a linkage, it has been possible to reproduce amyloid experimentally from materials derived solely from human brain tissue. Accordingly, reliable indicators are available for compounds that might be effective in treating cerebral amyloidosis; and it is possible to determine whether a group of compounds exists that block the conversion of a brain-localized precursor to cerebral amyloid (i.e., that display "anti-amyloid activity") at physiologically acceptable levels of the active agent.

A microscopic structure referred to as the dense microsphere is known to exist both in normal brain and in brain affected by Alzheimer's disease. See Averback, *Acta Neuropathol.* 61: 148-52 (1983); results confirmed by Hara, *J. Neuropath. Exp. Neurol.* (1986). Evidence for the existence of dense microspheres (DMS) comes from microscopic histological section studies of fixed whole brain tissue, where the dense microspheres are seen to have a proteinaceous central region ("DMS protein") surrounded by continuous membrane ("DMS membrane"). The dense microspheres are observed as randomly dispersed, very infrequent structures which occupy an estimated $10^{-9}$ or less of total brain volume, at a unit frequency roughly estimated at $10^{-14}$ or less relative to other definable brain structures such as mitochondria.

The extraction, purification, and characterization of isolated samples of DMS and the use of DMS material have been documented. See, for example, Averback, U.S. Pat. Nos. 4,919,915 and 4,816,416, the disclosures of which are incorporated by reference herein in their entirety.

It is well known that in the majority of cases, subjects with Alzheimer's disease and/or cerebral amyloidosis in general display symptoms on a quantitative basis Glessed, G, et al., "The association between quantitative measures of dementia and of senile change in the cerebral grey matter of elderly subjects," *British Journal of Psychiatry,* 114, pp 797-811 (1968); Tomlinson, B. E., et al., "Observations on the brains of non-demented old people," *Journal of the Neurological Sciences,* 7, pp 331-56 (1968); Tomlinson, B. E., et al., "Observations on the brains of demented old people," *Journal of the Neurological Sciences,* 11 pp 205-42 (1970); Corsellis, J. A. N., *Mental Illness and the Ageing Brain*" Oxford University Press, London (1962); Corsellis, J. A. N., "Ageing and the Dementias," *Greenfield's Neuropathology*, Edward Arnold, London, pp 796-848 (1976). Elderly subjects who have a small number of senile plaques are asymptomatic and are categorized by some experts as preclinical or by others as presymptomatic, or by still other authorities as normal variants. Thus, it is a common and perhaps normal feature of the elderly brain to have a low number of senile plaques, classified usually as within normal limits. However, when the amyloid plaque number is high, symptoms of dementia appear (see, references cited above). Therefore, a treatment mechanism is both useful and novel if it results in an individual at risk shifting from a high quantity senile cerebral amyloid plaque group to a low quantity senile cerebral amyloid plaque group.

DMS disruption does not commence before individual DMS reach a threshold size in the elderly or Alzheimer group. Averback, *Acta Nruropathol.* 61: 148-52 (1983). Therefore, a reduction in intact DMS size will delay the onset of DMS disruption, to the extent that the threshold size is not attained. There is therefore a need to provide methods for preventing DMS genesis and growth, which will prevent DMS enlargement and therefore significantly inhibit the autocatalytic phenomenon by the volume recruitment mechanism as described above.

There also is a need to provide methods that will also delay or prevent the initiation of the process which requires a minimal DMS size. Therefore, if DMS do not form at all, the particular cerebral amyloid formation which is induced by DMS disruption is totally prevented. If DMS size can be curtailed to an important extent (such as around 25% or more, for example), the DMS do not attain the threshold size for disruption, and therefore cerebral amyloid formation induced by DMS disruption can also be prevented.

SUMMARY OF THE INVENTION

It is therefore an object of the present invention to provide a method for impeding DMS formation and hence, in preventing and treating cerebral amyloidosis that is characterized by the presence of abnormal amounts of amyloid protein associated plaques (senile plaques).

It is also an object of the present invention to provide a method of treating β-amyloid diseases by the administration of agents that have in common an ability to inhibit, at physiologically acceptable levels, the growth, formation, and the eventual disruption of intact DMS.

In accordance with these and other objects of the invention, there is provided a method for preventing DMS genesis and growth that will prevent DMS enlargement and therefore significantly inhibit the autocatalytic exponential growth and disruption of DMS described in detail below. This method will also delay or prevent the initiation of the process which requires a minimal DMS size.

In accordance with an additional object of the invention, there is provided a method of curtailing the DMS size to an amount, such as around 25% or more, sufficient to prevent the DMS from attaining the threshold size for disruption. In accordance with this method, cerebral amyloid formation induced by DMS disruption is also prevented.

In accordance with an additional object of the invention, there is provided a composition that comprises a therapeutically effective amount of a compound that is capable of curtailing the DMS size to an amount, such as around 25% or more, sufficient to prevent the DMS from attaining the threshold size for disruption.

In accordance with these objectives, there are provided compositions and methods of treatment comprising administering compositions that include an effective amount of an antibody that is reactive against a component of DMS in combination with a pharmaceutically acceptable vehicle, whereby the antibody binds to the component and prevents or inhibits the growth and/or synthesis of DMS, and which prevents or inhibits the disruption of DMS.

Also in accordance with these objectives, there are provided compositions and methods of treatment comprising administering compositions that include an effective amount of at least one of the antisense oligonucleotides of the invention. The antisense oligonucleotides of the invention are complementary to portions of the mRNA coding for proteins that are at least partially responsible for DMS synthesis and growth, as well as DMS disruption and hence, administration of these antisense oligonucleotides prevents or inhibits the growth and/or synthesis of DMS, and prevents or inhibits the disruption of DMS. The compositions and methods of using the compositions typically include at least one of the antisense oligonucleotides in combination with a pharmaceutically acceptable sterile vehicle, as described in REMINGTON'S PHARMACEUTICAL SCIENCES: DRUG RECEPTORS AND RECEPTOR THEORY, (18th ed.), Mack Publishing Co., Easton Pa. (1990).

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description. Unless otherwise specified, the respective contents of documents cited in the following description are hereby incorporated by reference.

BRIEF DESCRIPTION OF THE DRAWINGS

FIG. 1 illustrates a nerve fiber matrix with one small DMS in the center.

FIG. 2 illustrates the same matrix with the DMS beginning to enlarge.

FIG. 3 illustrates the same matrix with the DMS continuing to grow and touch an adjacent nerve fiber which contains one small DMS.

FIG. 4 illustrates the same matrix whereby the small DMS on the adjacent nerve fiber has enlarged.

FIG. 5 illustrates a continuation of the enlargement of the DMS of FIG. 4.

FIG. 6 illustrates a continuation of the enlargement of the DMS of FIG. 5.

FIG. 7 illustrates the same initial matrix whereby the DMS in the center has enlarged and impinged on two additional adjacent nerve fibers, each containing one small DMS.

FIG. 8 illustrates the small DMS on the adjacent nerve fibers of FIG. 7 beginning to enlarge.

FIG. 9 illustrates a continuation of the enlargement of the DMS of FIG. 8.

FIG. 10 illustrates a continuation of the enlargement of the DMS of FIG. 9.

FIG. 11 illustrates the center DMS enlarging and disrupting to an even greater extent and impinging on 8 adjacent DMS-containing nerve fibers.

FIG. 12 illustrates the small DMS on the adjacent nerve fibers of FIG. 11 beginning to enlarge.

FIG. 13 illustrates a continuation of the enlargement of the DMS of FIG. 12.

FIG. 14 illustrates a continuation of the enlargement of the DMS of FIG. 13.

DETAILED DESCRIPTION OF THE PREFERRED EMBODIMENTS

Figure 1:
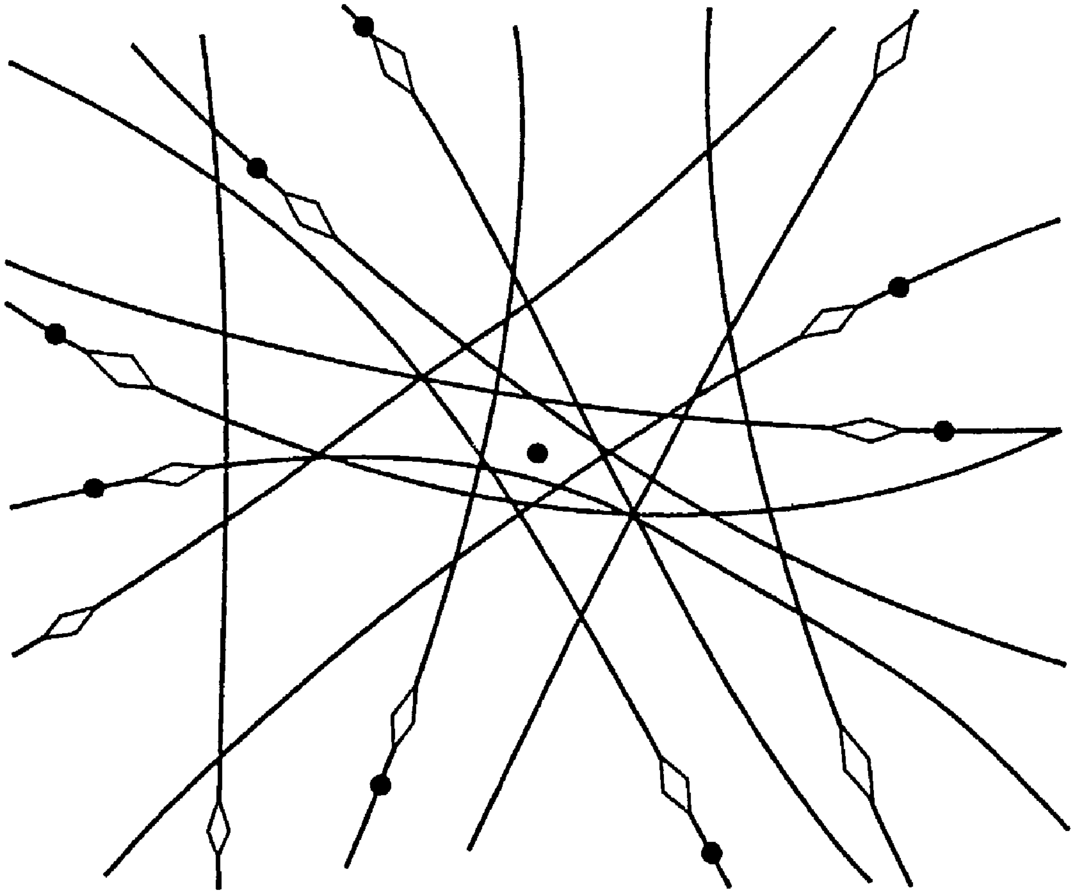
FIGS. 1-14 illustrate a simulation of DMS growth within nerve fibers and how the growth and disruption of one DMS can stimulate and bring about the growth and disruption of numerous DMS entities and adversely impact the nerve matrix.

It has now been discovered that the development of amyloid fibrils associated, for example, with the evolution of cerebral amyloidosis is tied to the unchecked disruption of DMS in vivo. The connection between DMS disruption and amyloid formation is evidenced in part by the observation that disrupted DMS treated with Congo Red stain display a red-green congophilic birefringence identical to that found in senile-plaque amyloid.

The usefulness of impeding cerebral amyloid formation is recognized and hence the usefulness of blocking the transformation of cerebral amyloid precursors, such as DMS, into amyloid is evident. The identification of harmful cerebral amyloid, harmful cerebral amyloid plaques, and harmful transformations of cerebral amyloid precursors including DMS into amyloid and amyloid plaques leads to useful methods to block or impede the transformations, and hence leads to less cerebral amyloid present in the brain. Therapy which inhibits DMS transformation to amyloid leads to less DMS-derived cerebral amyloid, and therefore less brain cerebral amyloid-derived injury.

A hitherto unrecognized and unanswered aspect of the problem of cerebral amyloid plaque formation as a result of DMS transformation and/or disruption concerns the initiating mechanism of DMS disruption to form cerebral amyloid plaques. If DMS did not exist, then it naturally follows that DMS transformation to cerebral amyloid would be eliminated; arrest of progression of DMS component accumulation and enlargement would provide less starting material and therefore less resultant cerebral amyloid from DMS transformation. DMS must reach a comparatively large size before transforming (Averback, *Acta Neuropathol.* 61: 148-52 (1983)). At smaller sizes they are stable in human brain and do not transform to amyloid in situ. If DMS were prevented from ever forming in human brain, or if DMS size was curtailed to an effective extent, the mechanism of individual DMS disruption and transformation to cerebral amyloid would be arrested or curtailed. If the overall mechanism of DMS transformation to cerebral amyloid was otherwise arrested, the effect would be useful via a mechanism quite distinct from blocking the molecular transformation of DMS components into cerebral amyloid. Mechanisms for blocking the molecular transformation of DMS components into cerebral amyloid are described in, for example, U.S. patent application Ser. No. 08/265,931, the disclosure of which is incorporated by reference herein in its entirety. In other words, blocking molecular transformation of DMS components to cerebral amyloid is used on DMS which have already begun the previously inevitable life cycle process of DMS intracellular growth followed by extracellular breakdown to cerebral amyloid. A useful and demonstrable method which prevents, impedes, or inhibits the genesis or origin or growth of DMS is hitherto unknown.

The present invention therefore serves to reduce DMS transformation to cerebral amyloid, i.e., by reducing the quantity of production or appearance of abnormal, demonstrably harmful molecules (amyloid) by preventing the genesis or growth of DMS, which in turn would, if growth were permitted, eventually disrupt and form amyloid senile plaques. In contrast to the present invention, DMS blocker therapy inhibits multiple individual DMS transformations to amyloid plaques by interrupting the transformations, at the individual level, of multiple individual DMS to multiple individual amyloid plaques after the DMS has enlarged to a sufficient size and disrupted.

While not intending to be bound by any theory, the present inventor believes that an important mechanism of initiation and promotion of DMS disruption consists of a distinctive type of autocatalytic phenomenon, whereby the disruption, degeneration, and evolution of an individual DMS into an individual cerebral amyloid plaque provides the stimulus for a group or field of multiple other individual DMS to in turn disrupt, degenerate and evolve as above in a recurring set of waves. This unchecked catalytic phenomenon thereby provides an exponential growth pattern, i.e., small, perhaps statistically insignificant differences (between individual brains) in starting numbers of disrupted DMS in situ evolve to statistically significant differences after adequate generations of the cycle. For example, for the sake of illustration, if all other factors were equal a starting group of 100 DMS would not be appreciably larger than a second starting group of, for example, 98 DMS. However, if each of the above DMS initiated over time 10 other DMS to disrupt then group 1 after 20 generations would have $2\times10^{20}$ more disrupted DMS than group 2. This difference obviously is statistically significant.

FIGS. 1-14 illustrate how one single DMS can stimulate the growth and disruption of 8 more DMS and, therefore, illustrate the exponential growth and disruption of DMS in brain. FIG. 1 shows one DMS in the center with about 12 nerve fibers in the near vicinity, which contain 8 other DMS (the DMS are shown in this Figure as a small dot ●). Hence, the round objects are DMS, the lines are nerve fibers and the empty triangles signify nerve cell bodies. In FIG. 1, the DMS in the center is stable.

Figure 2:
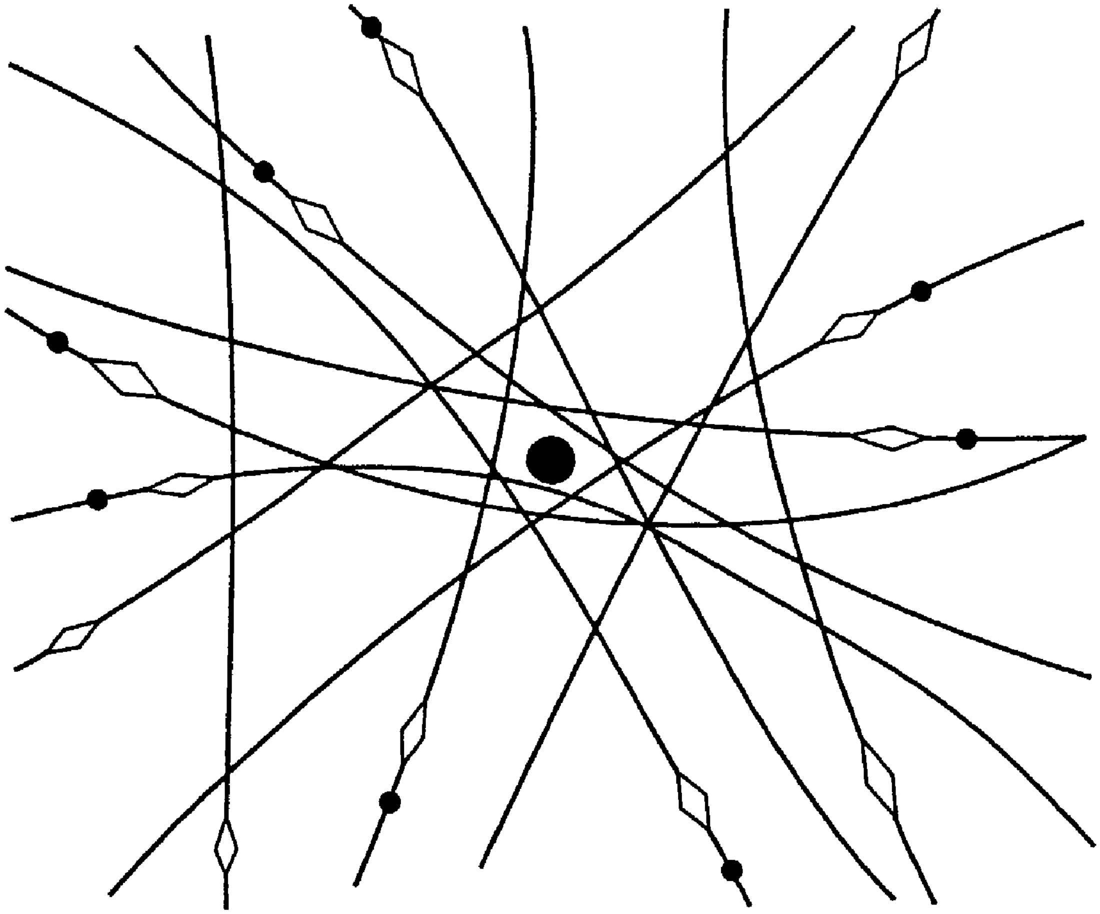
Figure 3:
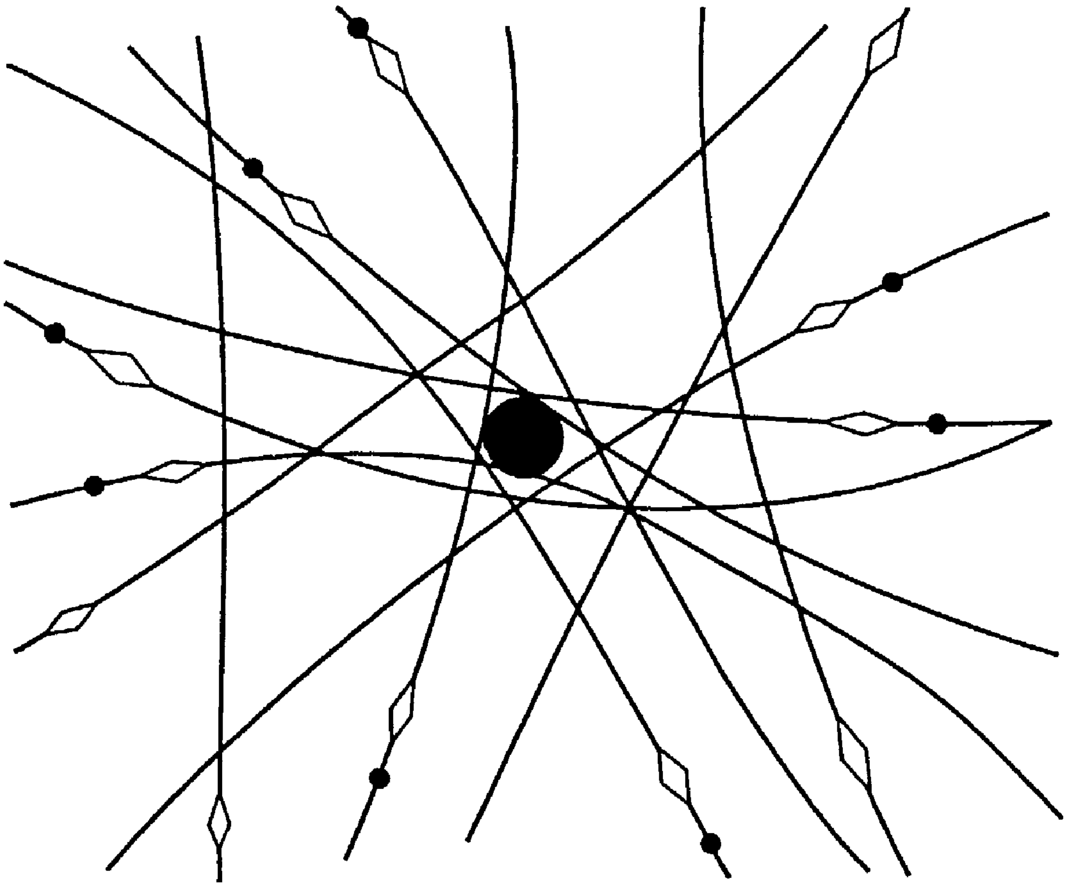
Figure 4:
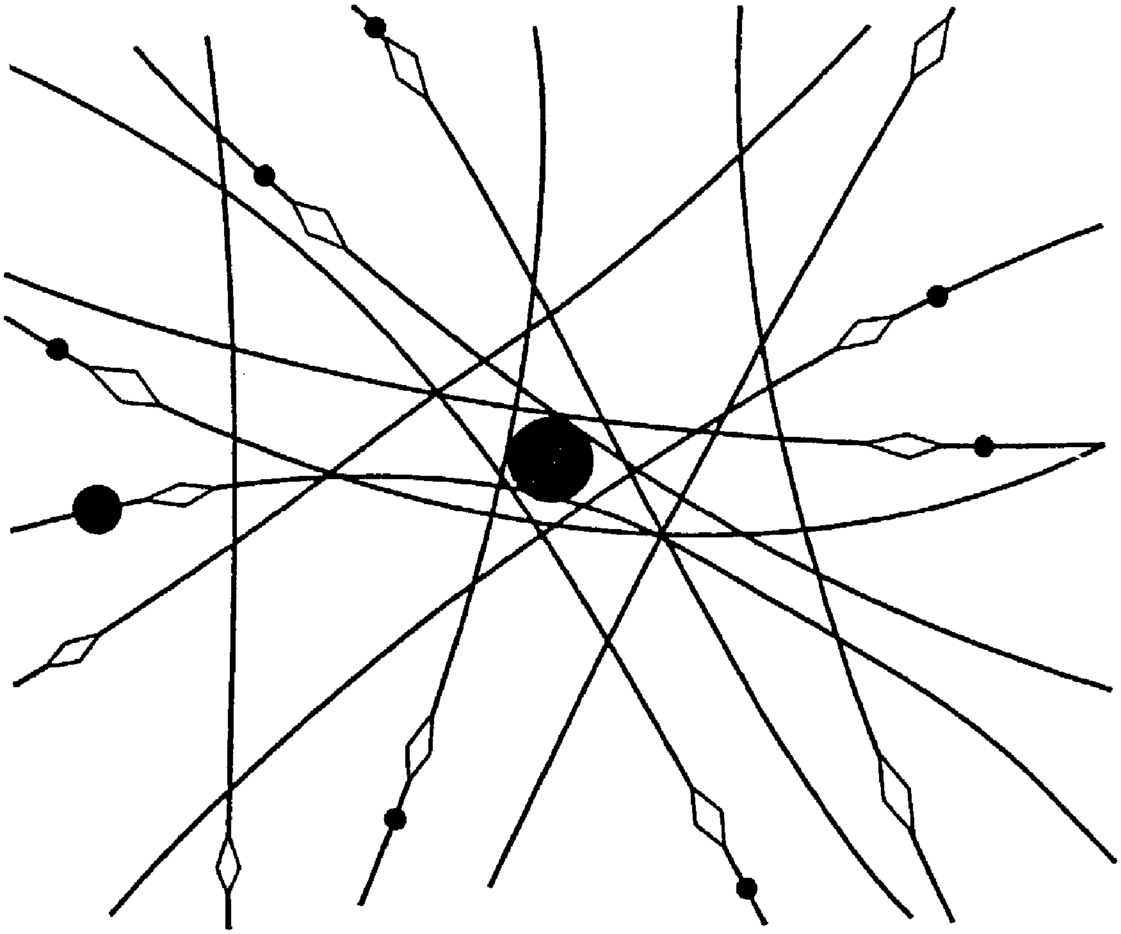
Figure 5:
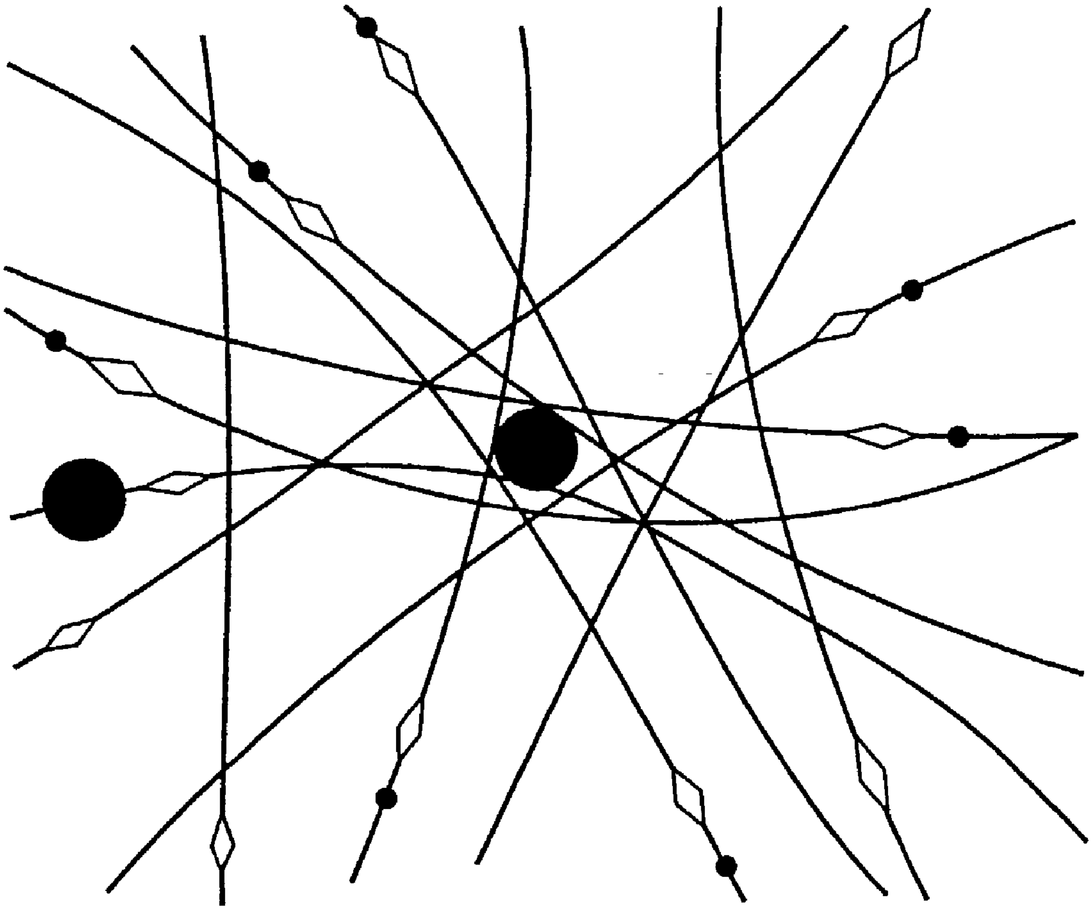
Figure 6:
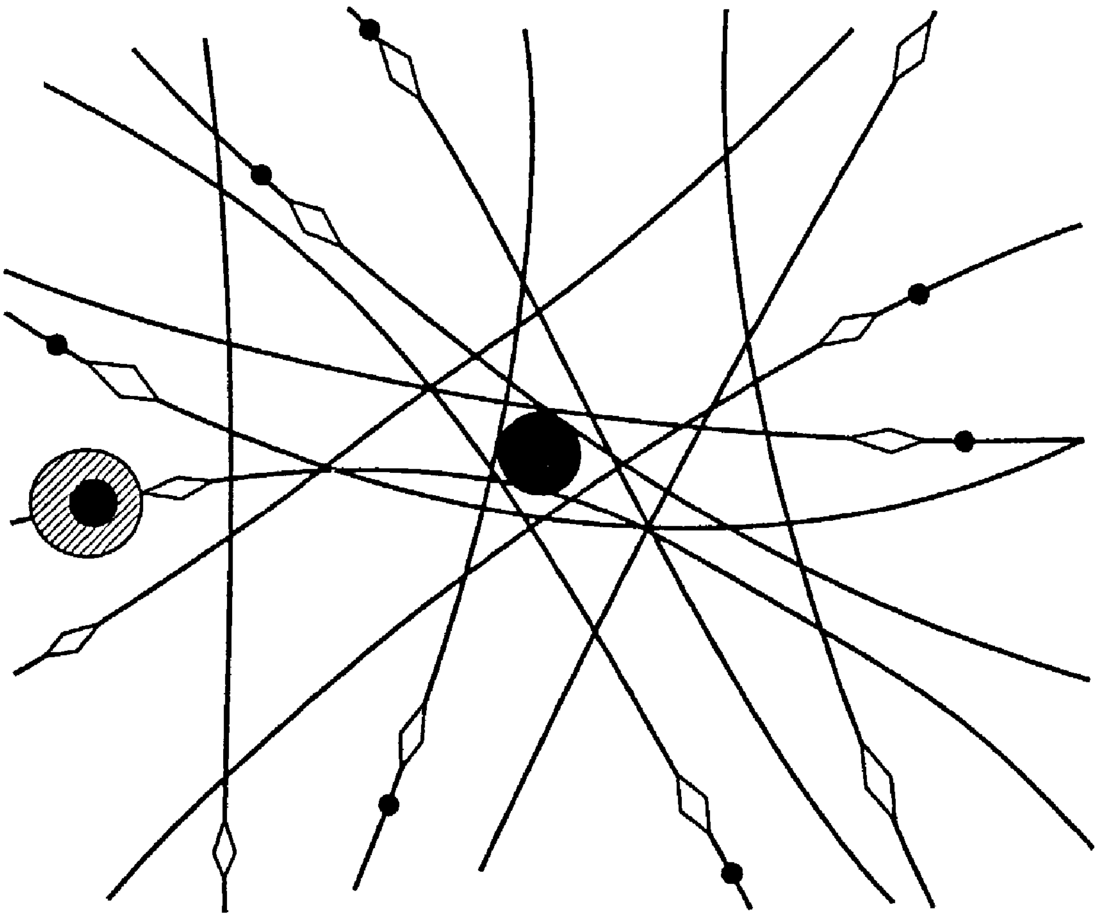
Figure 7:
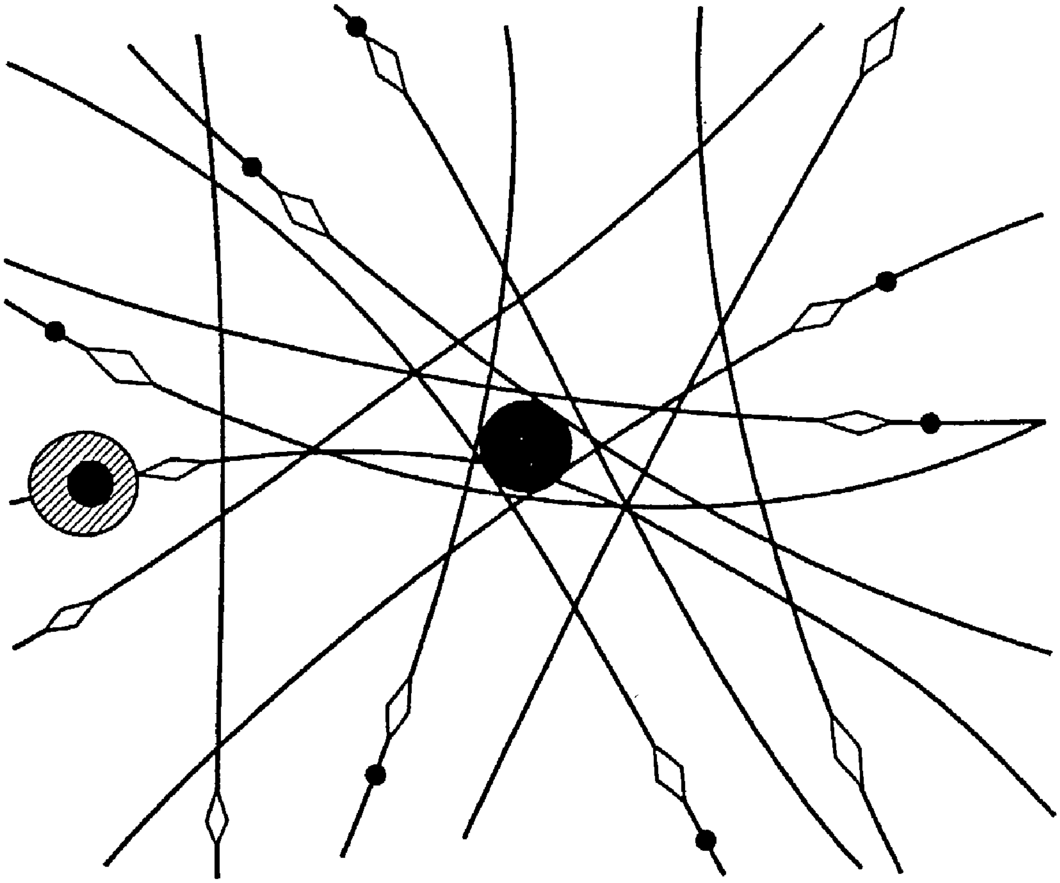
Figure 8:
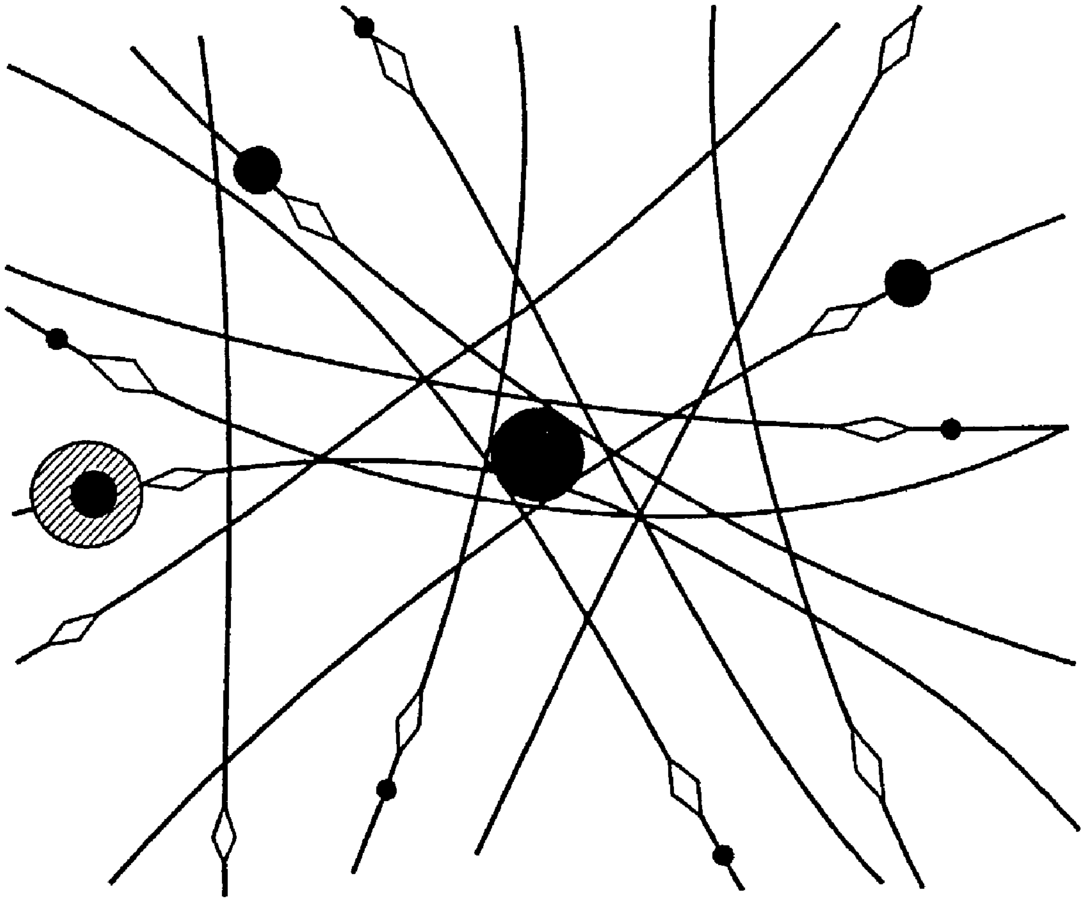
Figure 9:
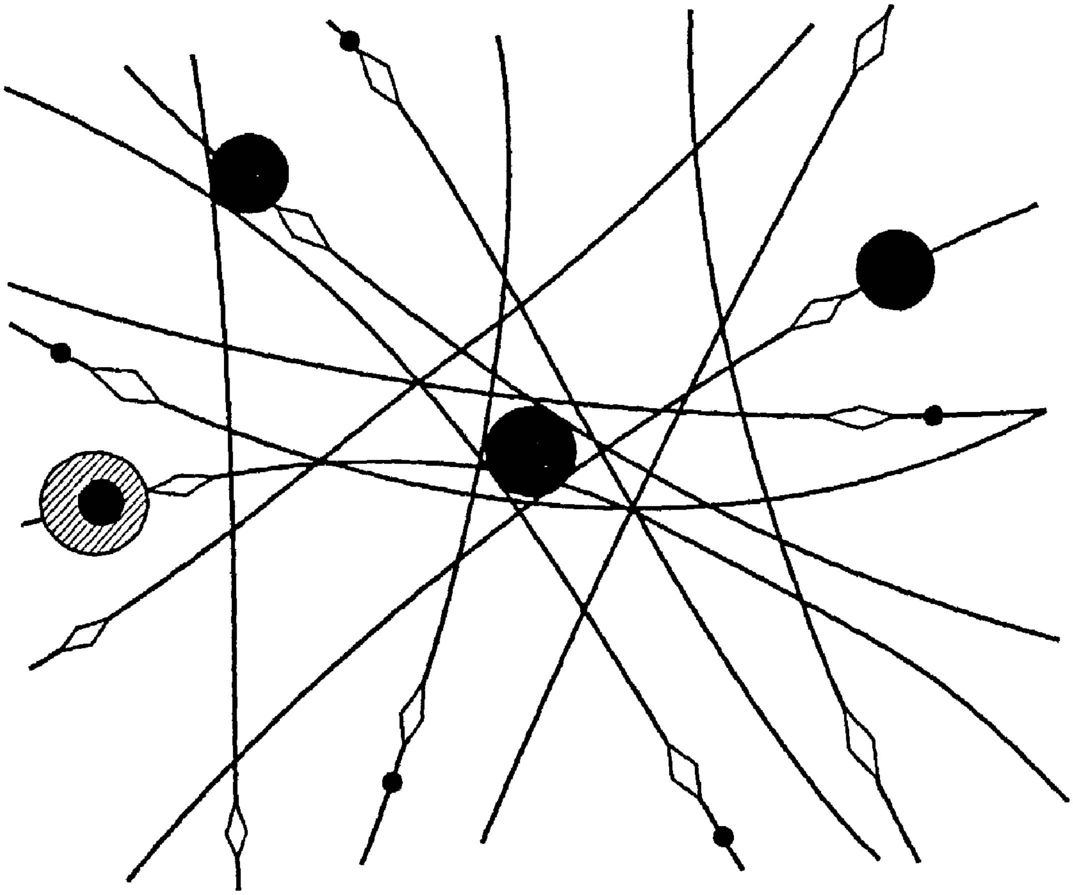
Figure 10:
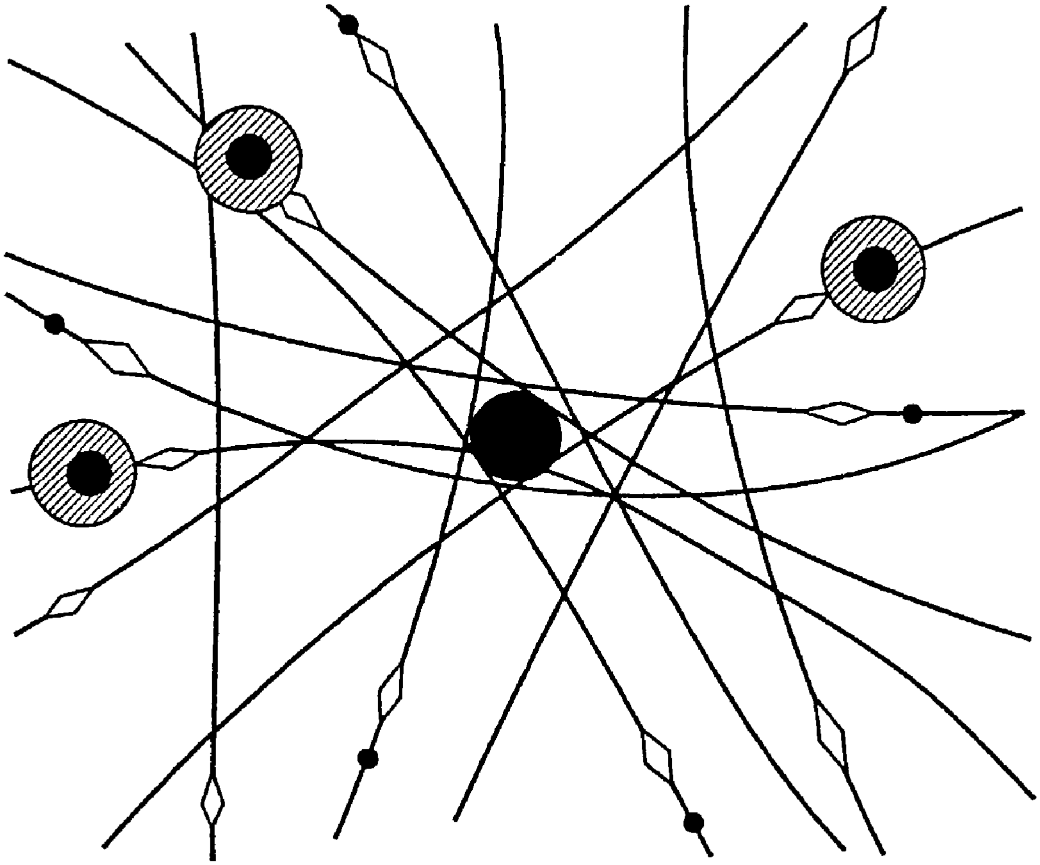

As shown in FIG. 2, the central DMS is beginning to enlarge and in FIG. 3, the central DMS has enlarged and touched one nerve fiber that contains another DMS. In FIGS. 4, 5 and 6, this second DMS begins to grow and enlarge and disrupt, while at the same time, the central DMS continues to grow and enlarge. In FIG. 7, the central DMS disrupts and impinges on two (2) additional DMS containing nerve fibers such that the DMS in these fibers, in FIGS. 8, 9 and 10, subsequently disrupt.

Figure 11:
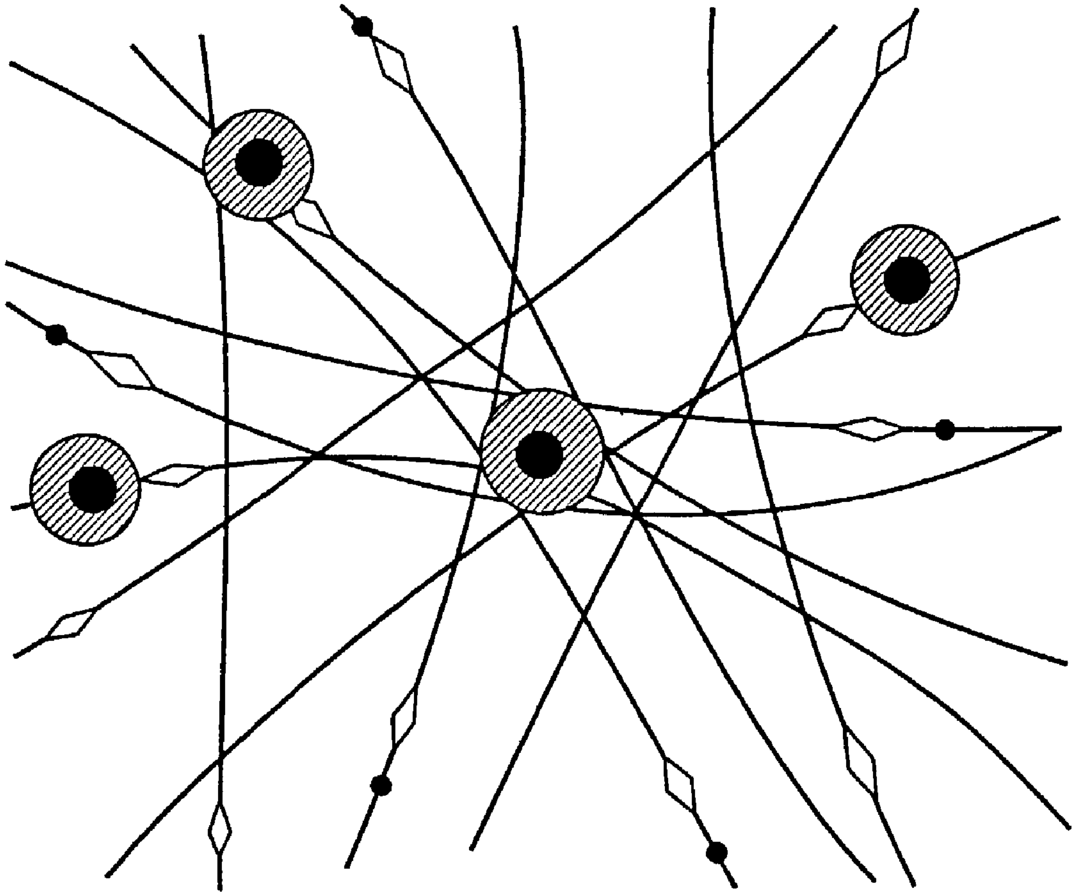
Figure 12:
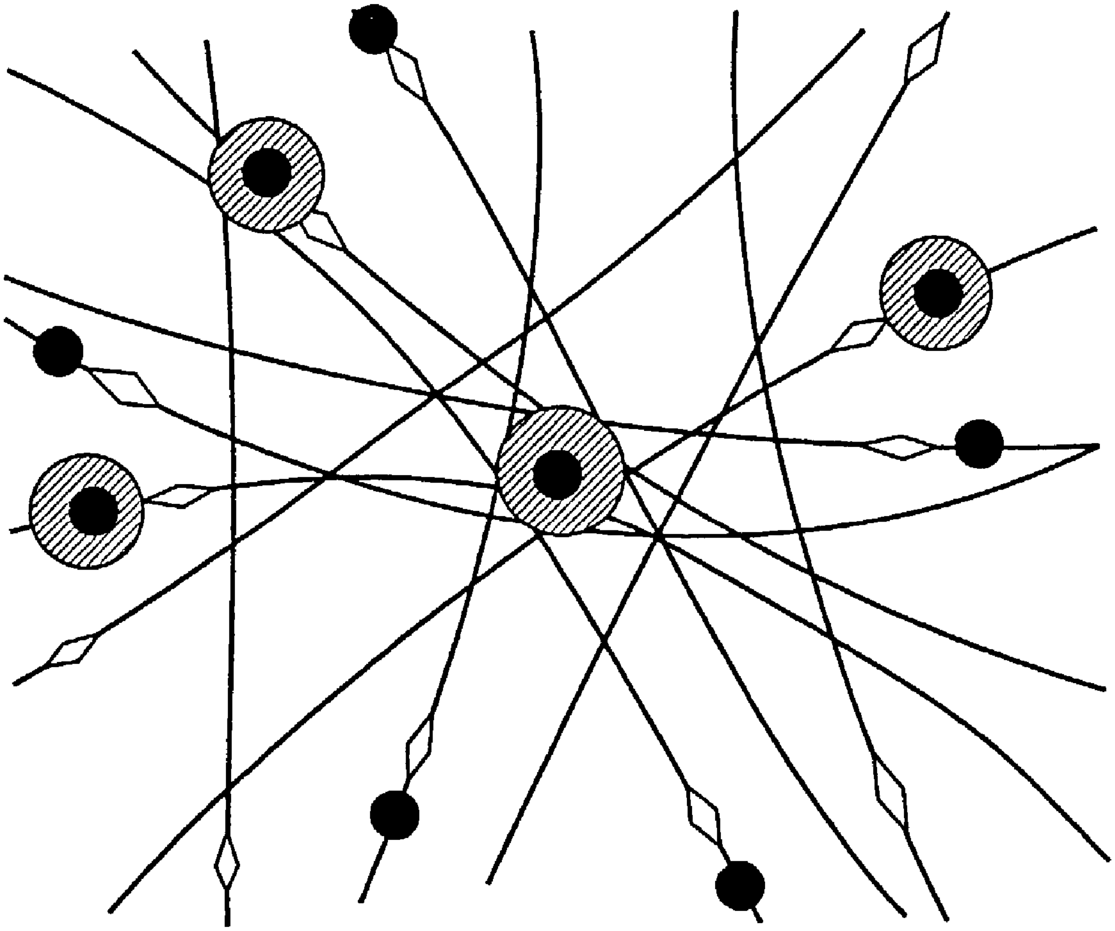
Figure 13:
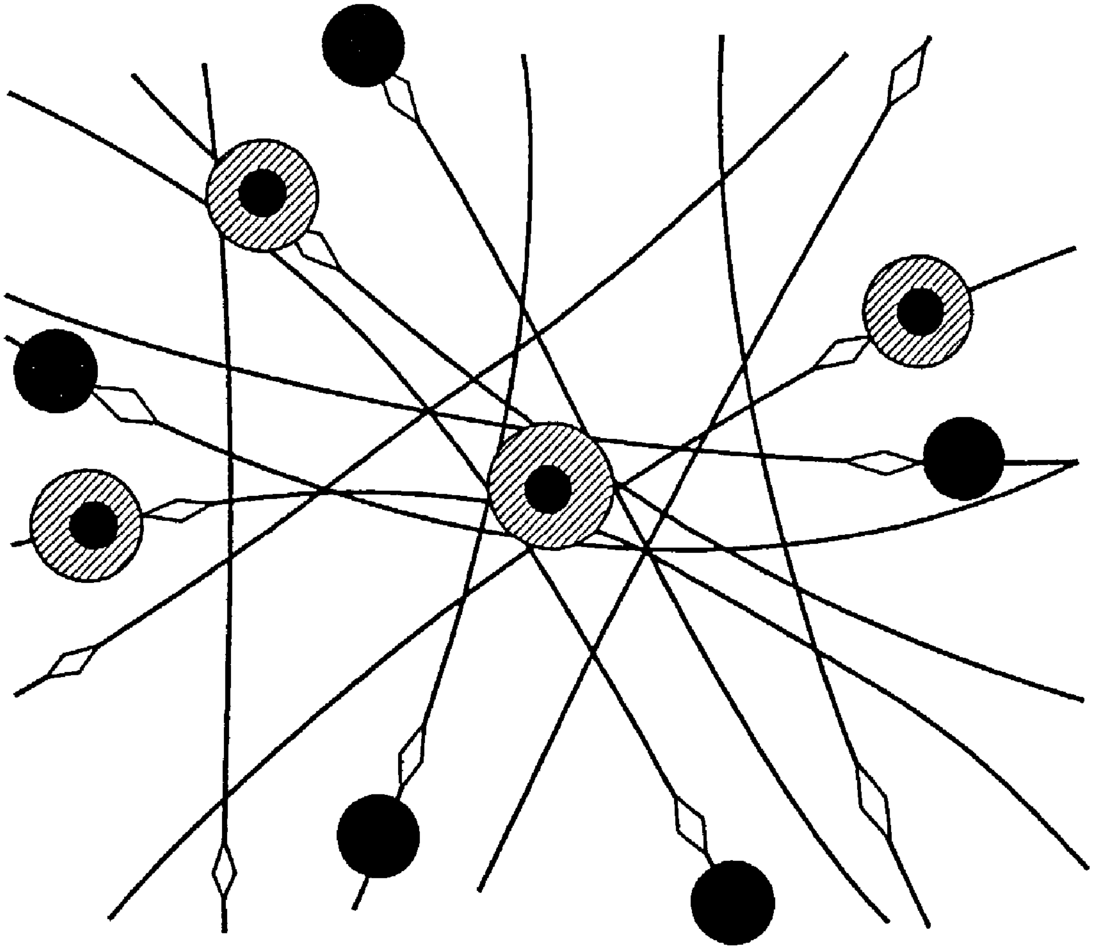
Figure 14:
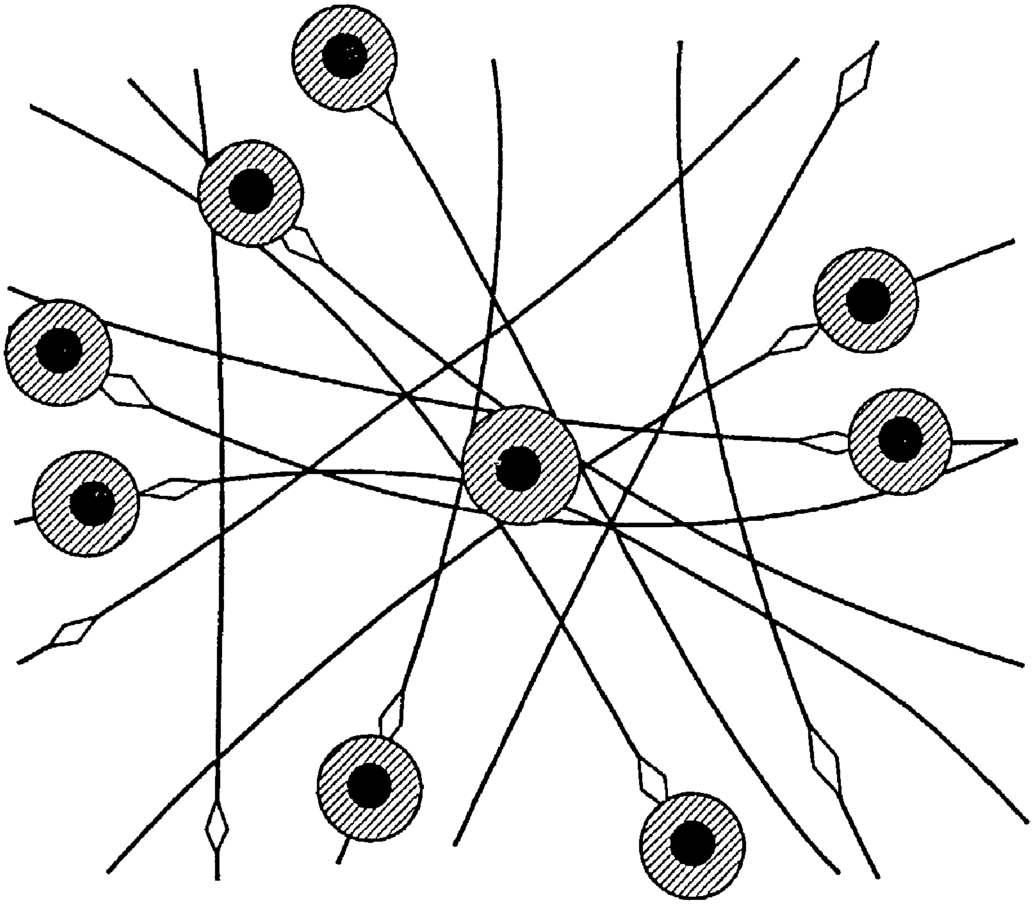

As shown in FIG. 11, the central DMS now has disrupted to an even greater extent and impinges on all DMS containing nerve fibers in the vicinity such that the DMS in these fibers, in FIGS. 12, 13 and 14 subsequently disrupt. A comparison of the DMS in FIGS. 3, 7 and 11 shows that a small disruption (FIG. 3) results in a total of one secondary disruption; a larger disruption (FIG. 7) results in a total of three secondary disruptions; and the largest disruption (FIG. 11) resulted in a total of eight secondary disruptions. The geometric progression of subsequent DMS disruption is readily apparent when the eight secondary disruptions each individually cause eight more disruptions for a total of 64, and then those 64 each cause eight more for a total of 512 disruptions, and so on.

The newly discovered mechanism whereby DMS disruption in certain foci facilitates DMS disruption located in other foci can also be conceived of as senile amyloid plaques leading to other senile amyloid plaques through the DMS intermediary mechanism. The connection between de novo DMS disruption and DMS disruption elsewhere in the brain is evidenced in part by several observations, such as:

A. Intact DMS are found within tiny nerve fibers and endings, and the latter are injured by the thousands when a DMS is disrupted and the ensuing injury reaction proceeds, as shown by electron microscopy of cerebral senile plaque lesions. The injury to the fiber which contains the DMS occurs at a different focus and explains the initiation of the DMS disruption. This is illustrated in FIGS. 1 to 6.

B. DMS disruption leading to further DMS disruption exponentially implies an accelerated course of senile plaque progression in comparatively younger subjects where nerve fiber density per unit volume is greater than in comparatively more elderly subjects. In other words, if there are more fibers per unit volume, then more fibers will pass through an area of disruption, and correspondingly more fibers containing intact DMS will be injured and thus more DMS will be injured as a result. It has been found, for example, that younger cases of cerebral amyloidosis or Alzheimer's disease run a more aggressive, faster course. Kono, K. et al., "*Is it useful to manage Alzheimer's disease as two clinical subtypes: Early onset and late onset subtypes*?", Basic, Clinical and Therapeutic Aspects of Alzheimer's and Parkinson's Diseases, Vol. 2, Plenum Press, N.Y., pp 143-146; Brandt, J., et al., "*Relation of Age of Onset and Duration of Illness to Cognitive Functioning in Alzheimer's disease*," NEUROPSYCHIATR. NEUROPSYCHOL. BEHAV. NEUROL., Vol. 2(2), pp. 93-101 (1989); Knesivich, J. W., et al., "*Aphasia, Family History, and the Longitudinal Course of Senile Dementia of the Alzheimer type*," PSYCHIATRY RES., Vol. 14, pp 255-263 (1984).

C. The total number of disrupted plus intact DMS in Alzheimer's disease brain has not been found to be significantly higher than in normal controls Averback, P, "Quantitative Correlations of Dense Microspheres and Senile Plaque in Alzheimer's Disease," *Neurology,* 32(2), A227, (1982) The exponential autocatalytic mechanism accounts simultaneously for: a) more numbers of disrupted DMS in disease compared to controls; b) the absence of a statistically significant difference in starting material quantity (numbers of intact DMS); and c) the sum of intact plus disrupted DMS being equal in Alzheimer's disease and normal individuals. In other words, Alzheimer's disease individuals and normal individuals start with roughly equal numbers of DMS, but the former group have a higher (faster) rate of transformation to disrupted DMS due to the autocatalytic D. Down's exponential mechanism.

Treatments that will reduce the number of starting DMS, inhibit the growth of DMS, or alternatively that will delay the time of initiation of the process of DMS disruption, will therefore impede significantly the kinetics of the autocatalytic phenomenon. Delay of the initiation can be achieved by 1) delay of the start of the whole process by, for example, inhibiting the growth of DMS, or also 2) by delay in terms of an individual DMS disruption. Retardation of the exponential process can also be effected by reducing the number of intact DMS recruited at each cycle by the DMS disruption process. A treatment that produces a small, perhaps insignificant, reduction in intact DMS recruitment per cycle will, as described above, produce in this exponential process a huge and important reduction in quantities of DMS disruption, with the result that the individual so treated can shift from the high quantity group to the low quantity group and thereby remain asymptomatic. Quantitative reduction of the rate of recruitment implies that certain individual DMS will have delay of onset of disruption.

The extent of DMS recruitment from the DMS disruption and brain injury process is proportional to the number of DMS containing fibers that are injured by the DMS disruption. A large hippocampal cortical senile plaque in an individual with Alzheimer's disease measures up to a diameter of 100 micrometers, (volume 525,000 cubic microns), and thus, if the diameter were reduced to 80 micrometers with a corresponding volume of 268,200 cubic microns and injured fibers, the number of DMS recruited would be reduced by approximately half. A smaller and perhaps statistically insignificant reduction in intact DMS recruitment will, by the exponential dynamic described above, produce a huge and statistically significant reduction in the total number of DMS which are disrupted after a given number of generations of secondary DMS disruption. This almost insignificant volume reduction in disrupted DMS induced cerebral amyloid will thereby allow, for a given point in time, a shift from high quantity cerebral amyloid plaques to low quantity, and thereby prevent the subject from becoming symptomatic at that given point in time (see FIGS. 6-10).

It has also been discovered that compounds which are effective in inhibiting DMS formation or growth can be used to treat cerebral amyloidosis, including Alzheimer's disease. Particularly effective in this regard are compounds that act on DMS protein synthesis, for example, via intracellular RNA binding, (e.g., antisense oligonucleotides) so as to prevent or limit the DMS growth.

The DMS microspheric bodies employed according to the present invention are derived from mammalian brain tissue and are characterized, in essentially homogeneous form, by a range of diameters from about 0.1 μm to about 15 μm, by the above-mentioned outer membrane/proteinaceous core structure of DMS, and by certain stainability properties. (In this regard, "homogeneous" means that the DMS represent the only structure discernible in the subject composition at the light-microscopic level.) For example, the microspheric bodies of the present invention are homogeneously electron-dense when stained with osmium and lead, and can be visualized by thin-section electron microscopy; under optical microscopic examination, they appear eosinophilic and phloxinophilic, and are nonbirefringent when stained with Congo Red. When the microspheric bodies of the present invention are disrupted, a material is produced that displays congophilic birefringence; that is, when stained with Congo Red, the material becomes optically anisotropic to the extent of splitting an incident light wave into two waves with mutually perpendicular vibrational planes.

DMS are spherical, membrane-bounded, intracellular structures, about 0.1 to 15 μm in diameter, that are found in human and other mammalian brains. More specifically, the normal location for DMS is in gray-matter neuropil, where the spherical structures are enclosed in tiny, neuronal cellular processes. DMS are solitary, non-perikaryal and non-confluent, and are not found in cerebellum or in white matter. With regard to inter-DMS distances, the spatial distribution of DMS in gray matter regions is random. Compositions of DMS in homogeneous form can be produced by extraction, according to U.S. Pat. No. 4,816,416, to give homogeneous samples of globular bodies.

Chemical analyses of DMS samples by methods such as gel electrophoresis, high performance liquid chromatography, mass spectrometry, and amino sequence analysis have revealed numerous protein components in addition to amyloid and amyloid precursor proteins. By making an inhibitor to one or more of these DMS components, and reducing or eliminating their synthesis, the DMS growth is significantly retarded. For this purpose, methods such as those which employ the principle of directed antisense RNA directed to selected DMS proteins is preferred. The use of antisense oligonucleotides is known in the art. For a review, see Stein et al., *Cancer Research* 48: 2659 (1988).

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules or oligonucleotides are capable of binding to mRNA molecules, resulting in an inhibition of mRNA translation.

The binding of antisense RNA molecules to target mRNA molecules results in hybridization arrest of translation. Paterson, et al., *Proc. Natl. Acad. Sci. USA,*: 74 4370 (1987). Thus, a suitable antisense RNA oligonucleotide would have a sequence that is complementary to all or part of a mRNA species encoding a protein that is necessary for cellular function. For example, antisense RNA molecules can be used to inhibit the translation of mRNAs encoding actin, tubulin, ubiquitin, ubiquitin conjugating enzyme, ubiquitin carrier protein or elongation factors. DNA molecules containing genes that encode known protein sequences can be isolated using standard techniques. Moreover, DNA molecules containing genes encoding the nucleotide sequences Nos. 1-7 listed below can be synthesized using the given nucleotide sequences. In light of the state of the art, skilled artisans, armed with the nucleotide sequences Nos. 1-7 below, are capable of synthesizing antisense RNA oligonucleotides directed to mRNAs that encode these proteins which are believed to be at least partially responsible for DMS growth and development, and eventual disruption.

For an antisense oligonucleotide to be therapeutically useful it is desirable that it exhibit not only the ability to inhibit DMS synthesis, growth and/or disruption, but that it also exhibit low cellular toxicity. Suitable toxicity measurements are well known in the art, and the skilled artisan is capable of assessing the toxicity of any of the antisense oligonucleotides described herein. Antisense oligonucleotides can be tested for in vivo efficacy and safety in an animal model system. A preferred animal model is one in which the animal is infected with DMS whereby the DMS undergoes an analogous synthesis, growth and disruption cycle as in humans, and should produce clinical symptoms analogous to those observed in human Alzheimer's disease such as dementia and the like. Several animal models exist such as primates, dogs and certain strains of mice whereby these animals, when injected intracerebrally with DMS, undergo a similar synthesis, growth or disruption cycle as that found in humans.

As used in this disclosure the term "oligonucleotide" encompasses both oligomeric nucleic acid moieties of the type found in nature, such as the deoxyribonucleotide and ribonucleotide structures of DNA and RNA, and man-made analogues which are capable of binding to nucleic acids found in nature. The oligonucleotides of the present invention can be based upon ribonucleotide or deoxyribonucleotide monomers linked by phosphodiester bonds, or by analogues linked by methyl phosphonate, phosphorothioate, or other bonds. They may also comprise monomer moieties which have altered base structures or other modifications, but which still retain the ability to bind to naturally occurring DNA and RNA structures. Such oligonucleotides may be prepared by methods well-known in the art, for instance using commercially available machines and reagents available from Perkin-Elmer/Applied Biosystems (Foster City, Calif.).

As recognized by those skilled in the art, inhibition of the synthesis and growth of proteins or other components that are widespread in the body such as actin and the like, are less useful due to toxicity and side effects. Proteins of a comparatively restricted nature, without known widespread adult functional significance, are preferred due to the absence or minimum of toxicity and side effects. Proteins with multiple isoforms, or proteins whose inhibition of synthesis and/or growth is non-toxic despite functional significance also are preferred.

Antisense RNA and corresponding genes coding for the expression of the following amino sequences are preferred for DMS growth prevention or inhibition:

```
(SEQ ID NO:1)
1:   Ile-Leu-Asp-Leu-Gly-Ile-Thr-Gly-Pro-Glu-Gly-
     His-Val-Leu-Ser-Arg-Pro-Glu-Glu-Val-Glu-Ala-
     Glu-Ala-Val-Asn-Lys;

(SEQ ID NO:2)
2:   Ile-Ala-Val-Gly-Ser-Asp-Ala-Asp-Leu-Val-Ile-
     Trp-Asp-Pro-Asp-Ser-Val-Lys;

(SEQ ID NO:3)
3:   Ile-Val-Asn-Asp-Asp-Gln-Ser-Phe-Tyr-Ala-Asp-
     Ile-Tyr-Met-Glu-Asp-Gly-Leu-Ile-Lys;

(SEQ ID NO:4)
4:   Asn-Ile-Ile-Leu-Glu-Glu-Gly-Lys-Asp-Ile-Leu-
     Val-Gly-Asp-Val-Gly-Gln-Thr-Val-Asp-Asp-Pro-
     Tyr-Ala-Thr-Thr-Phe-Val;

(SEQ ID NO:5)
5:   Gly-Ile-Val-Asp-Gln-Ser-Gln-Gln-Ala-Tyr-Gln-
     Glu-Ala-Phe-Glu-Ile-Ser-Lys;

(SEQ ID NO:6)
6:   Val-Asn-Pro-Thr-Val-Phe-Phe-Asp-Ile-Ala-Val-
     Asp-Gly-Glu-Pro-Leu-Gly-Arg; and
```

-continued

```
(SEQ ID NO:7)
7:   Thr-Val-Pro-Pro-Ala-val-Thr-Gly-Ile-Thr-Phe-
     Leu-Ser-Gly-Gly-Glu-Ser-Glu-Glu-Glu-ala-Ser-
     Ile-Asn-Leu-Asn-Ala-1le-Asn-Lys.
```

Those skilled in the art are capable of modifying the aforementioned amino acid sequences to a given degree of homology without adversely affecting the activity and usefulness in the present invention. With the given modifications, skilled artisans likewise are capable of synthesizing antisense RNA and corresponding genes coding for the expression of the modified amino acid sequences, as well as antibodies that bind to portions of the genes coding for the expression of the modified amino acid sequences.

While protein synthesis inhibitors and other inhibitors for DMS components can be provided by those skilled in the art after identification of the DMS components, the usefulness of such inhibitors is restricted by the inevitable toxicity if the components have any other function(s) in the body. For example, inhibition of key synthetic enzymes in oxidative or glycolytic metabolic pathways would probably be unacceptably toxic or fatal. As a further example, inhibition of proteins which are not synthesized or not used (apart from DMS incorporation) in important ways in the adult would not be fatal or unacceptably toxic. Such unimportant components could be, for example, unique to the DMS or highly restricted on a quantitative basis to the DMS, or as yet a further example, could be active in the embryo or fetus or child, but not in the adult. As yet a further example, such a component could be active or present elsewhere in the body apart from the brain but could be selectively inhibited by a brain specific antagonist delivery system, or alternatively, its inhibition could have side effects that were minimal and justifiable in comparison to the beneficial effects outlined herein.

It has now been discovered that from the total group of DMS components, certain unexpected components are not known to have other significant functions in the adult human, and therefore, an unanticipated group of protein synthetic inhibitors can thus be used to eliminate or reduce cerebral amyloid formation induced by DMS disruption by the mechanisms of: a) no DMS formation; and/or b) decreased DMS starting material leading to decreased overall DMS based cerebral amyloid burden; and/or c) significant inhibition of the autocatalytic recruitment phenomenon of DMS disruption.

The aforementioned peptide sequences of the DMS components determined as above can be used to determine the DNA sequence encoding the component. Methods for carrying out this determination are well known in the art. See, for example Sambrook et al., MOLECULAR CLONING: A LABORATORY MANUAL, Second Edition, (Cold Spring Harbor Laboratory Press, Cold Spring Harbor, N.Y. 1989).

In a preferred embodiment of the present invention, the peptide sequences are used to design degenerate oligonucleotide primers for polymerase chain reactions. Each degenerate primer set will preferably contain every possible DNA sequence encoding the corresponding peptide sequences. Primer sets are prepared in both the sense and antisense orientation. Suitable oligonucleotide primers can be synthesized using commercial synthesizers, such as those supplied by Applied Biosystems (Foster City, Calif.). In a particularly preferred embodiment, the primers include additional nucleotide sequences containing restriction endonuclease cleavage sites. The presence of such sites allows for the directional cloning of PCR products into suitable cloning vectors after treatment with an appropriate restriction enzyme. See Finney, "Molecular Cloning of PCR Products" in CURRENT PROTOCOLS IN MOLECULAR BIOLOGY, Ausubel et al. Eds. (John Wiley & Sons, New York, 1987) p. 15.7.1.

Template DNA for the PCR can be prepared from an appropriate parasitic organism using methods well known in the art. See Sambrook et al., supra. In a preferred embodiment, parasites are crushed under liquid nitrogen and mRNA is extracted using a commercially available kit (Pharmacia, Piscataway, N.J.). In a particularly preferred embodiment, parasite samples are taken from several different stages of the parasite life cycle, and DNA prepared separately from each sample.

The mRNA preparation can then be used as a template for cDNA synthesis using poly(dT) or random hexamer primers by standard techniques. See Sambrook et al., supra. In a particularly preferred embodiment, cDNA synthesis is carried out using a commercially available kit (Pharmacia).

The cDNA can then be used directly for PCR using the method of Saiki et al., *Science* 239: 487 (1988). The cDNA also is used to prepare a cDNA library by standard methods. See Sambrook et al., supra. In a particularly preferred embodiment, the cDNA is packaged into bacteriophage particles using a commercially available kit (Promega, Madison, Wis.). The packaged cDNA is then transfected into *E. coli* to produce a cDNA library.

In an alternative preferred embodiment, genomic DNA from a parasite can be used as the template DNA for the PCR. Genomic DNA can be prepared by standard methods, for example, using Triazol™, a commercial reagent available from Life Technologies, Inc. (Gaithersburg, Md.). In a particularly preferred embodiment, samples of ground ticks, prepared as above are extracted into a Tris-saline-EDTA-SDS buffer and the extract treated with RNAse A and Proteinase K to digest RNA and proteins. After phenol: chloroform extraction, the DNA is ethanol precipitated by standard methods and resuspended in TE buffer.

The PCR can then be used to prepare double stranded DNA molecules to probe the cDNA library and the genomic DNA for the gene(s) encoding the DMS components. In a preferred embodiment, degenerate primers are prepared corresponding to the termini of the longest peptide sequence determined by peptide sequencing. In a particularly preferred embodiment, primers are used in a PCR with first strand cDNA as template to amplify the DNA encoding the peptide. PCR is carried out under standard conditions. See Sakai et al., supra.

PCR amplification products are analyzed by polyacrylamide gel electrophoresis using standard methods. If an amplification product of the expected size (based on the peptide sequence) is found, the product is digested with appropriate restriction enzymes, ligated into a cloning vector and cloned by standard methods. See Sambrook et al, supra. In a preferred embodiment, clones are sequenced to verify that sequences according to the expected peptide sequence are present.

Once the DNA sequence encoding the peptide is known, it can be used to prepare non-degenerate primers corresponding to that sequence, again containing restriction enzyme recognition sequences to aid in cloning of DNA products. These primers are used in combination with degenerate primers corresponding to other peptide sequences to generate PCR amplification products which can be cloned and then analyzed as above. By these means, fragments of the gene sequence of the DMS component can be determined. Alternative methods for carrying out this PCR analysis include use of the 5' or 3' RACE methods using commercially available kits, such as those manufactured by Life Technologies (Gaithersburg, Md.) or Clontech (Palo Alto, Calif.). Primers for this method are selected according to the manufacturer's directions.

Gene fragments prepared as above are excised from the cloning vector by restriction enzyme digestion, labeled with $^{32}P$ by conventional methods and used as probes to identify the complete gene encoding the DMS component from within a cDNA library. In a preferred embodiment, the probe is chosen such that it is long enough to ensure hybridization specificity, while remaining short enough to allow reasonable rates of hybridization to the target gene.

Screening of the cDNA library is carried out by conventional methods. See Sambrook et al, supra. cDNA clones which hybridize to the probe are purifed and their sequences determined. To facilitate sequencing, nested deletions in the clones can be created using standard protocols, or by commercially available kits such as Erase-a-base (Promega, Madison, Wis.) or The Deletion Factory (Life Technologies, Gaithersburg, Md.), following the manufacturer's instructions. The sequences obtained are analyzed for the presence of open reading frames by conventional methods and to check if the entire gene sequence has been found. In a preferred embodiment, cDNA libraries are prepared by both random hexamer and poly (dT) priming from parasite samples taken from several different stages of the parasite life cycle, and are used to maximize the chances of finding the complete coding sequence of the desired gene.

As a further variation on the above method of using antisense oligonucleotides to inhibit DMS component synthesis and growth, inhibition of DMS component incorporation into DMS will inhibit DMS growth. Therefore, certain compounds which bind to DMS components after the latter are synthesized (e.g., antibodies to the DMS components) will interfere with intact DMS growth. This group of DMS component binding agents are thus DMS inhibitors which function by inhibiting postsynthetic DMS component protein assembly into intact DMS. These agents also have selective specificity as defined by the target protein assembly inhibition, where postsynthetic inhibition of certain DMS proteins such as important functional proteins is less useful due to toxicity and side effects.

The method of the present invention for treating cerebral amyloidosis is used with subjects in whom amyloid formation is anticipated. The treatment can be applied, for example, to those who are at risk of developing cerebral amyloid, as in senile plaques, including the elderly, nondemented population and patients with the diagnoses listed above under the cerebral-amyloidosis rubric. In addition to its use in these patient groups, such prophylactic therapy can be effected, pursuant to the present invention, to inhibit or prevent less severe forms of brain-function decline correlated with the formation of smaller amounts of disrupted DMS in elderly, nondemented subjects in whom dementia, due to the diseases listed above under the cerebral-amyloidosis rubric, is not expected.

Compounds within the present invention that display anti-amyloid activity at an in-tissue concentration of about $10^{-5}$ M or less, e.g. between about $10^{-5}$ and $10^{-6}$ M or less, e.g. between $10^{-5}$ and $10^{-6}$ M, can be administered to such subjects orally, rectally, via nasal route, parenterally (including by skin or other routes, in spray or aerosol form, or via inhalation. A compound within the present invention can thus be administered in a pharmaceutically-acceptable carrier therefor, such as physiological saline solution.

Compounds of the present invention are particularly preferred that, in addition to possessing DMS disruption inhibiting activity in the aforementioned concentration range, also are nontoxic at an appropriate dosage level, having a satisfactory duration of effect, and display an adequate ability to cross the blood-brain barrier. In this regard, U.S. Pat. No. 4,540,564 discloses an approach for enhancing blood-brain barrier-penetrating ability by attaching a centrally acting drug species to a reduced biooxidizable, lipoidal form of a dihydropyridine pyridinium salt redox carrier. Also particularly preferred are compounds that have specific, selective binding affinity for DMS components.

Determining a pharmaceutically-effective amount of a compound administered in accordance with the present invention entails standard evaluations of pharmacokinetic data and clinical efficacy. See, e.g., GOODMAN AND GILMAN'S THE PHARMACOLOGICAL BASIS FOR THERAPEUTICS (7th ed.). Thus, the above-described in vivo animal testing will provide the basis for a range of dosages and dosage schedules to be assessed clinically in humans. An assessment in this regard would generate pharmacokinetic data, for example, regarding bioavailability, absorption metabolism, serum levels and excretion.

Such data would be evaluated against clinical data obtained concurrently from neurobehavior testing, for example, memory testing and testing of cognitive function and from clinical medical assessment if a dosage halts progression of deterioration in clinical parameters for a symptomatic patient, i.e., a subject diagnosed as suffering from cerebral amyloidosis, that dosage should also have a prophylactic effect in the elderly, nondemented population. In addition, a pharmaceutical composition within the present invention could be employed to ameliorate or prevent a decline in brain function, associated with amyloid formation, that is less than dementia, e.g., where the subject does not require supervision or nursing care.

Prophylactic therapy in the aforementioned population could be effected, pursuant to the present invention, for all persons of normal brain function who fall within a prescribed age group, for example, 65- or 70- to 75-years old. Alternatively, prophylactic therapy could be applied to nondemented persons of any age who, while displaying normal brain function are identified via diagnostic testing that reveals evidence of DMS disruption in the brain.

Diagnostic testing of this sort can be conducted by assaying, immunologically or otherwise, for the presence of DMS components such as DMS membrane in biological samples. DMS protein or fragments thereof may be present in biological samples not derived from brain tissue, e.g. samples of serum, spinal fluid and other bodily fluids. Testing can also be directed to detection in a subject of antibodies against one or more DMS components. In addition, prophylactic therapy according to the present invention can be administered to the nondemented population on the basis of other factors, suggesting a risk for dementia, which are revealed by radiological or diagnostic imaging, genetic testing, electroencephalography or other means.

The following test paradigms illustrate ways in which DMS material, as described above, can be employed routinely, according to the present invention, in identifying anti-amyloidosis agents within the aforementioned class of compounds.

EXAMPLE ONE

COMPARATIVE EXAMPLE

Polyacrylamide gel electrophoresis, high performance liquid chromatography, mass spectrometry and amino acid sequence analysis of DMS fractions showed the present of actin in DMS preparations. Actin is a well known major protein component of the body with widespread functions in many tissues such as muscle and nerve. Actin synthetic inhibition would therefore be toxic throughout the body and is not a suitable method of inhibiting DMS based cerebral amyloid formation.

EXAMPLE TWO

Polyacrylamide gel electrophoresis, high performance liquid chromatograph, mass spectrometry and amino acid sequence analysis of DMS fractions showed the presence of a protein component with the following amino acid sequence:

```
(SEQ ID NO:1)
1:   Ile-Leu-Asp-Leu-Gly-Ile-Thr-Gly-Pro-Glu-Gly-
     His-Val-Leu-Ser-Arg-Pro-Glu-Glu-Val-Glu-Ala-
     Glu-Ala-Val-Asn-Lys;
```

This protein does not at present have known important function in the adult human brain and, therefore, inhibition of its synthesis is a suitable method for inhibiting the DMS based cerebral amyloid formation.

EXAMPLE THREE

Other proteins identified in DMS provide other protein inhibition methods for reducing DMS based cerebral amyloid formation. Other examples include:

```
(SEQ ID NO:2)
2:   Ile-Ala-Val-Gly-Ser-Asp-Ala-Asp-Leu-Val-Ile-
     Trp-Asp-Pro-Asp-Ser-Val-Lys;

(SEQ ID NO:3)
3:   Ile-Val-Asn-Asp-Asp-Gln-Ser-Phe-Tyr-Ala-Asp-
     Ile-Tyr-Met-Glu-Asp-Gly-Leu-Ile-Lys;

(SEQ ID NO:4)
4:   Asn-Ile-Ile-Leu-Glu-Glu-Gly-Lys-Asp-Ile-Leu-
     Val-Gly-Asp-Val-Gly-Gln-Thr-Val-Asp-Asp-Pro-
     Tyr-Ala-Thr-Thr-Phe-Val;

(SEQ ID NO:5)
5:   Gly-Ile-Val-Asp-Gln-Ser-Gln-Gln-Ala-Tyr-Gln-
     Glu-Ala-Phe-Glu-Ile-Ser-Lys;

(SEQ ID NO:6)
6:   Val-Asn-Pro-Thr-Val-Phe-Phe-Asp-Ile-Ala-Val-
     Asp-Gly-Glu-Pro-Leu-Gly-Arg; and

(SEQ ID NO:7)
7:   Thr-Val-Pro-Pro-Ala-val-Thr-Gly-Ile-Thr-Phe-
     Leu-Ser-Gly-Gly-Glu-Ser-Glu-Glu-Glu-ala-Ser-
     Ile-Asn-Leu-Asn-Ala-Ile-Asn-Lys.
```

Like the protein of example 2, these proteins do not at present have known important functions in the adult human brain and therefore, inhibition of their synthesis is a suitable method for inhibiting the DMS based cerebral amyloid formation.

EXAMPLE FOUR

The proteins listed in Examples 2 and 3 and numbered 1-7, respectively, can be purified upon identification using conventional purification techniques. Monoclonal and polyclonal antibodies to these proteins then can be manufactured using techniques known to those skilled in the art, such as those described in U.S. Pat. No. 5,231,170. Upon purification of the antibodies, they then can be administered to a- mammal suffering from or susceptible to Alzheimer's disease whereby the antibodies will serve to inhibit the syn thesis, growth, multiplication and/or disruption of DMS and thereby inhibit the DMS based cerebral amyloid formation. Patients with Alzheimer's disease may go from a symptomatic stage to an asymptomatic stage, and patients susceptible to Alzheimer's disease will attain a lower risk of disease.

While the invention has been described in detail by reference to particularly preferred embodiments and examples, those skilled in the art recognize that various modifications can be made to the invention without departing from the spirit and scope thereof. All documents that have been discussed in this specification are incorporated by reference herein in their entirety.

What is claimed is:

1. A method of inhibiting the formation of amyloid plaques in mammalian brain comprising administering to a patient in need thereof a pharmaceutical composition consisting essentially of a monoclonal antibody that binds to SEQ ID NO: 1.

* * * * *